(12) United States Patent
Vogel et al.

(10) Patent No.: US 8,778,333 B2
(45) Date of Patent: *Jul. 15, 2014

(54) INJECTABLE MICROSPHERES FOR TISSUE CONSTRUCTION

(75) Inventors: Jean-Marie Vogel, Lincoln, MA (US); Egisto Boschetti, Croissy-sur-Seine (FR)

(73) Assignee: Biosphere Medical, Inc., South Jordan, UT (US)

(*) Notice: Subject to any disclaimer, the term of this patent is extended or adjusted under 35 U.S.C. 154(b) by 951 days.

This patent is subject to a terminal disclaimer.

(21) Appl. No.: 12/009,181

(22) Filed: Jan. 16, 2008

(65) Prior Publication Data

US 2008/0118569 A1    May 22, 2008

Related U.S. Application Data

(63) Continuation of application No. 10/220,984, filed as application No. PCT/US01/08528 on Mar. 15, 2001, now Pat. No. 7,338,657.

(60) Provisional application No. 60/190,542, filed on Mar. 20, 2000.

(51) Int. Cl.
| | | |
|---|---|---|
| A61K 35/12 | (2006.01) |
| A61K 9/14 | (2006.01) |
| A61K 9/50 | (2006.01) |
| A61F 2/02 | (2006.01) |
| C12N 11/08 | (2006.01) |
| C12N 5/071 | (2010.01) |
| C12N 5/074 | (2010.01) |
| C12N 5/0775 | (2010.01) |
| C12N 5/07 | (2010.01) |

(52) U.S. Cl.
USPC .......... 424/93.7; 424/520; 424/489; 424/501; 424/423; 424/426; 435/180; 435/372; 435/395; 435/396

(58) Field of Classification Search
None
See application file for complete search history.

(56) References Cited

U.S. PATENT DOCUMENTS

| | | |
|---|---|---|
| 3,223,083 A | 12/1965 | Cobey |
| 3,919,411 A | 11/1975 | Glass |
| 4,192,784 A | 3/1980 | Brown et al. |
| 4,197,846 A | 4/1980 | Bucalo |
| 4,413,070 A | 11/1983 | Rembaum |
| 4,452,916 A | 6/1984 | Boschetti |
| 4,500,658 A | 2/1985 | Fox |
| 4,525,358 A | 6/1985 | Baltes |
| 4,622,362 A | 11/1986 | Rembaum |
| 4,786,555 A | 11/1988 | Howard, Jr. |
| 4,803,075 A | 2/1989 | Wallace |
| 4,999,188 A | 3/1991 | Solodovnik et al. |
| 5,007,940 A | 4/1991 | Berg |
| 5,158,573 A | 10/1992 | Berg |
| 5,202,352 A | 4/1993 | Okada et al. |
| 5,226,914 A | 7/1993 | Caplan |
| 5,298,570 A | 3/1994 | Tahara |
| 5,306,500 A | 4/1994 | Rhee |
| 5,324,775 A | 6/1994 | Rhee |
| 5,336,263 A | 8/1994 | Ersek |
| 5,344,452 A | 9/1994 | Lemperle |
| 5,451,406 A | 9/1995 | Lawin |
| 5,470,911 A | 11/1995 | Rhee |
| 5,550,187 A | 8/1996 | Rhee |
| 5,550,188 A | 8/1996 | Rhee |
| 5,578,709 A | 11/1996 | Woiszwillo |
| 5,633,001 A | 5/1997 | Agerup |
| 5,635,215 A | 6/1997 | Boschetti |
| 5,648,100 A | 7/1997 | Boschetti |
| 5,667,778 A | 9/1997 | Atala |
| 5,695,480 A | 12/1997 | Evans et al. |
| 5,716,404 A | 2/1998 | Vacanti |
| 5,792,478 A | 8/1998 | Lawin |
| 5,830,708 A | 11/1998 | Naughton |
| 5,843,987 A | 12/1998 | Rajagopalan |
| 5,855,610 A | 1/1999 | Vacanti |
| 5,855,615 A | 1/1999 | Bley |
| 5,885,829 A | 3/1999 | Mooney |
| 5,906,934 A | 5/1999 | Grande |
| 5,919,707 A | 7/1999 | Banks |
| 5,922,025 A | 7/1999 | Hubbard |
| 5,981,825 A | 11/1999 | Brekke |
| 6,086,863 A | 7/2000 | Ritter |
| 6,214,331 B1 | 4/2001 | Vanderhoff |
| 6,224,893 B1 | 5/2001 | Langer et al. |
| 6,238,335 B1 | 5/2001 | Silverman et al. |
| 6,335,028 B1 | 1/2002 | Vogel |
| 6,436,424 B1 | 8/2002 | Vogel |

(Continued)

FOREIGN PATENT DOCUMENTS

| | | |
|---|---|---|
| EP | 0251695 A2 | 1/1988 |
| EP | 0648480 A2 | 4/1995 |

(Continued)

OTHER PUBLICATIONS

U.S. Appl. No. 09/528,989, Not Published, Vogel et al.

(Continued)

*Primary Examiner* — David M Naff
(74) *Attorney, Agent, or Firm* — Stoel Rives LLP

(57) ABSTRACT

The present invention relates to injectable compositions comprising biocompatible, hydrophilic, non-toxic and substantially spherical microspheres associated with stem cells useful for tissue construction and generation. The invention also relates to methods of tissue construction and generation, for the treatment of various tissue damage and defects, using the injectable compositions.

27 Claims, No Drawings

(56) References Cited

U.S. PATENT DOCUMENTS

| | | | |
|---|---|---|---|
| 6,660,301 | B1 | 12/2003 | Vogel |
| 6,680,046 | B1 | 1/2004 | Boschetti |
| 6,790,456 | B2 | 9/2004 | Vogel |
| 6,911,219 | B2 | 6/2005 | Matson |
| 7,060,298 | B2 | 6/2006 | Vogel |
| 7,338,657 | B2 | 3/2008 | Vogel |
| 7,591,993 | B2 * | 9/2009 | Boschetti |
| 8,142,815 | B2 * | 3/2012 | Vogel et al. ............ 424/489 |
| 2002/0068089 | A1 | 6/2002 | Vogel et al. |
| 2002/0187172 | A1 | 12/2002 | Reb et al. |
| 2003/0211083 | A1 | 11/2003 | Vogel et al. |
| 2003/0211165 | A1 | 11/2003 | Vogel |
| 2003/0212002 | A1 | 11/2003 | Haskell-Luevano et al. |
| 2003/0212022 | A1 | 11/2003 | Vogel et al. |
| 2004/0091425 | A1 | 5/2004 | Boschetti |
| 2004/0096514 | A1 | 5/2004 | Vogel |
| 2005/0025708 | A1 | 2/2005 | Vogel |
| 2005/0158393 | A1 | 7/2005 | Reb |
| 2006/0039896 | A1 | 2/2006 | Kleinsek et al. |
| 2006/0063732 | A1 | 3/2006 | Vogel |
| 2006/0251582 | A1 | 11/2006 | Reb |
| 2008/0033366 | A1 | 2/2008 | Matson |
| 2008/0039890 | A1 | 2/2008 | Matson |
| 2008/0220077 | A1 | 9/2008 | Vogel |
| 2009/0117196 | A1 | 5/2009 | Boschetti |
| 2009/0186094 | A1 | 7/2009 | Vogel |
| 2010/0119572 | A1 | 5/2010 | Boschetti |
| 2011/0033508 | A1 | 2/2011 | Vogel |
| 2011/0182998 | A1 | 7/2011 | Reb |

FOREIGN PATENT DOCUMENTS

| | | |
|---|---|---|
| EP | 0713707 A1 | 5/1996 |
| EP | 0811373 A2 | 12/1997 |
| FR | 2378808 A1 | 8/1978 |
| FR | 2784580 | 4/2000 |
| GB | 2 144 327 A | 3/1985 |
| JP | 6056676 | 3/1994 |
| WO | WO 89/07455 A1 | 8/1989 |
| WO | WO 92/06702 | 4/1992 |
| WO | WO 92/06702 A1 | 4/1992 |
| WO | WO 92/21327 | 12/1992 |
| WO | WO93/15721 | 8/1993 |
| WO | WO 94/21299 A1 | 9/1994 |
| WO | WO 96/12510 | 5/1996 |
| WO | WO 96/12510 A1 | 5/1996 |
| WO | WO 98/52543 | 11/1996 |
| WO | WO 96/39464 | 12/1996 |
| WO | WO 99/31167 | 6/1999 |
| WO | WO 99/34829 | 7/1999 |
| WO | WO 99/44643 | 9/1999 |
| WO | WO 00/23054 | 4/2000 |
| WO | WO 2010/062678 | 6/2010 |

OTHER PUBLICATIONS

Beaujeux et al., "Trisacryl Gelatin Microspheres for Therapeutic Embolization, II: Preliminary Clinical Evaluation in Tumors and Arteriovenous Malformations," *Am J Neuroradiol*, 17:541-548 (1996).

Chowdhury et al., "Use of Microbeads for Cell Transplantation," *Advanced Research on Animal Cell Technology*, pp. 315-327, (1989).

Langer et al., "Tissue Engineering," *Science*, 260:920-926 (1993).

Laurent et al., "Trisacryl Gelatin Microspheres for Therapeutic Embolization, I: Development and In Vitro Evaluation," *Am J Neuroradiol*, 17:533-540 (1996).

Levine, et al., "Microcarrier Cell Culture: New Methods for Research-Scale Application," *Somatic Cell Genetics*, 3:149-155 (1977).

Obrenovitch et al., "Microcarrier Culture of Fibroblastic Cells on Modified Trisacryl Beads," *Biol. Cell*, 46:249-256 (1982).

Owen, "Marrow Stromal Stem Cells,"*J Cell Sci*, Suppl., 10:63-76 (1988).

Van Vezel, "Growth of Cell-Strains and Primary Cells on Micro-Carriers in Homogeneous Culture," *Nature*, 216:64-65 (1967).

U.S. Appl. No. 12/695,080, filed Jan. 27, 2010, Reb et al.

U.S. Appl. No. 12/534,070, filed Jul. 31, 2009, Vogel et al.

Beaujeux, "Trisacryl Gelatin Microspheres for Therapeutic Embolization. II: Preliminary Clinical Evaluation in Tumors and Arteriovenous Malformations" *AJNR* 17(3):541-548 (1996).

Berman, "Comparative Cost Analysis of Collagen Injection and Fascia Lata Sling Cystourethropexy for the Treatment of Type III Incontinence in Women," *J. Urology*. 157:122-124 (1997).

Boschetti, "Synthese et copolymerisation de nouveaux monomeres acryliques diiodes et triiodes." *Bull. Soc. Chim.Fr.*. 4:669-677 (1996) (with English Abstract).

Boschetti, "Polyacrylamide Derivatives to the Service of Bioseparations," *J. Biochem-Biophys. Meth.*, 19:21-36 (1989).

Boschetti, Microspheres for Biochromatography and Biomedical Applications; Part I, Preparation of Microbeads *In*: Microspheres, Microencapsulation and Liposomes, John Wiley & Sons, Arshady R., Ed. 2: 171-189 (1999).

Brown, "Syntheses and copolymerizations of new water-soluble polyiodinated acrylic monomers," *Makromol. Chem., Rapid Commun.* 6:503-507 (1985).

Cherksey, "Adrenal Chromaffin Cells on Microcarriers Exhibit Enhanced Long-Term Functional Effects When Implanted into the Mammalian Brain," *IBRO*, 657-664 (1996).

Chowdhury., "Use of Microbeads for Cell Transplantation," *In*: Advanced Research on Animal Cell Technology, A.O.A. Miller ed., Kluwers Acad. Press, 315-327(1989).

Communication Pursuant to Article 96(2) EPC issued on Dec. 3, 2004 in connection with European Application No. 01922415.3.

Dixit, "Hepatocyte immobilization on pHEMA microcarriers and its biologically modified forms" *Cell Transplantation* 1:391-399 (1992).

Edgerton, "Indications for and Pitfalls of Soft Tissue Augmentation with Liquid Silicone" Plast. Reconstr. Surg., 58:157-163 (1976).

Eppley., "A Potential Biomaterial Composite for Dermal and Subcutaneous Augmentation," *Annals of Plastic Surgery*, 32(5):463-468 (1994).

Gerhart, "Biomechanical Optimization of a Model Particulate Composite for Orthopaedic Applications," *Journal of Orthopedic Research*, 4:76-85 (1986).

Glowacki, "Comparison of Multinucleated Cells Elicited in Rats by Particulate Bone, Polyethylene, or Polymethylmethacrylate," *Journal of Bone and Mineral Research*, 1(4):327-331 (1986).

Goldring, "Multinucleated Cells Elicited in Response to Implants of Devitalized Bone Particles Possess Receptors for Calcitonin," *Journal of Bone and Mineral Research*, 3(1):117-120 (1988).

Goodman, "The Effects of Bulk *VERSUS* Particulate Polymethylmethacrylate on Bone," *Clin. Orthop. Relat. Res.*, 232:255-262 (1988).

Herschorn, "Followup of Intraurethal Collagen for Female Stress Urinary Incontinence," *J. Urology*, 156:1305-1309 (1996).

Herzog, "Urinary Incontinence: Medical and Psychosocial Aspects," *Ann. Rev. Gerontol. Geriatrics*, 9(Chap. 3):74-119 (1989).

Horák, "Hydrogels in Endovascular Embolization. I. Spherical Particles of Poly(2-hydroethyl methacrylate) and Their Medico-biological Properties" *Biomaterials*, 7:188-192 (1986).

Horák, "Hydrogels in Endovascular Embolization. II. Clinical Use of Spherical Particles" *Biomaterials*, 7:467-470 (1986).

Horák, "Hydrogels in Endovascular Embolization. III. Radiopaque Spherical particles. Their Preparation and Properties" *Biomaterials*, 8:142-144 (1987).

Johnson, "Outcome of Respiratory Symptons After Anti-reflux Surgery on Patients With Gastroesphageal Reflux Disease," *Archives of Surgery*, 131:489-492 (1996).

Khullar, "GAX Collagen in the Treatment of Urinary Incontinence in Elderly Women: A Two Year Follow Up," *British J. Obstetrics & Gynecology*, 104:96-99 (1996).

Klutke, "Early Results With Antegrade Collagen Injection for Post-Radical Prostatectomy Stress Urinary Incontinence," *J. Urology*, 156:1703-1706 (1996).

(56) References Cited

OTHER PUBLICATIONS

Kondo, "Bladder Neck Support Prosthesis: A Nonoperative Treatment for Stress or Mixed Urinary Incontinence," *J. Urology*, 157:824-827 (1996).
Krukowski, "Charged Beads Stimulate Bone Formation" 34th Annual Meeting Orth. Res. Soc. (Feb. 1988).
Langer, "Tissue Engineering," *Science*, 260:920-926, May 14, 1993.
Laurent, "Trisacryl Gelatin Microspheres for Therapeutic Embolization, I: Development and In Vitro Evaluation," *Am. J. Neuroradiol.*, 17:533-540 (1996).
Laurent, "Etude Histologique de Plusieurs Materiaux D'Embolisation et D'Un Nouveau Type de Materiel Spherique et Adhesif," *Innov. Tech. Biol. Med.* 10: 358-366 (1989).
Laurent, "Etude Histologique de Plusieurs Materiaux D'Embolisation et D'Un Nouveau Type de Materiel Spherique et Adhesif," *Innov. Tech. Biol. Med.* 10: 358-366 (1989). (English-language Translation).
Leonard, "Treatment of Urinary Incontinence in Children by Endoscopically Directed Bladder Neck Injection of Collagen," *J. Urology*, 156:637-641 (1996).
Lemperle, "PMMA Microspheres for Intradermal Implantation: Part I. Animal Research," *Ann Plast Surg*, 26:57-63 (1991).
Lemperle, "PMMA-Microspheres (Artecoll) for Long-Lasting Correction of Wrinkles: Refinements and Statistical Results," *Aesthetic Plastic Surgery*, 22:356-365 (1998).
Lemperle, "Soft Tissue Augmentation with Artecoll: 10-Year History, Indications, Techniques, and Complications," *Dermatol Surg*, 29:573-587 (2003).
Levesque, "Ten-Year Experience With the Artificial Urinary Sphincter in Children," *J. Urology*, 156:625-628 (1996).
Levine, "Microcarrier Cell Culture: New Methods for Research-Scale Application," *Somatic Cell Genetics*, 3:149-155 (1977).
Lima, "Combined use of enterocystoplasty and a new type of artificial sphincter in the treatment of urinary incontinence," *J. Urology* 156:622-624 (1996).
Mazza, "Polymer Design in Dye Chromatography: From the definition of monomers to the evaluation of polymeric supports," in Protein-Dye Interactions: Developments and Applications, Vijayalakshmi M.A. ed., Elsevier Appl. Sciences, Elsevier Sci. Publ. Ltd., pp. 126-136 (1989).
McClelland, "Evaluation of Antibody Class in Response to Bovine Collagen Treatment in Patients With Urinary Incontinence," *J. Urology* 155:2068-2073 (1996).
Millikan. "Long Term Safety and Efficiency with Fibre( in the Treatment of Cutaneous Scars", *J Dermatol Surg Oncol*, 15:837-846 (1989).
Morhenn, "Phagocytosis of Different Particulate Dermal Filler Substances by Human Macrophages and Skin Cells," *Dermatol Surg*, 28:484-490 (2002).
Nebel, "Symptomatic Gastroesophageal Reflux: Incidence and Precipitating Factors," *Am. J. Dig. Dis.*, 21,(11):953-956 (1976).
Obrenovitch, "Microcarrier Culture of Fibroblastic Cells on Modified Trisacryl Beads," *Biol. Cell.*, 46:249-256 (1983).
Ott, "Biocompatibility of Microscopic Beads of PMMA (Polymethyl Methacrylate) in Rat Skin," Doctoral Dissertation, Johann Wolfgang Goethe University, Frankfurt am Main, Germany (41 pgs.) (1988).
Owen, "Marrow Stromal Stem Cells," *J Cell Sci, Suppl.*, 10:63-76, 1988.
Perez, "Submucosal Bladder Neck Injection of Bovine Dermal Collagen for Stress Urinary Incontinence in the Pediatric Population," *J. Urology*, 156:633-636 (1996).
Remacle, "Cultures of Preadipocytes on Microparticles Their Properties of Adhesion Proliferation and Differentation," *Manuscript from University Catholique de Louvain, Laboratiore de Biologie Cellulaire*, 1-33 (1997).
Reynolds, "Influence of pathophysiology, severity, and cost on the medical management of gastroesophageal reflux disease," *Am. J. Health-Sys. Pharm.* 53:S5-S12 (1996).

Stinson, "Tissue Reaction Induced in Guinea-Pigs by Particulate Polymethylmethacrylate, Polythene and Nylon of the Same Size Range," *British Jour. Exp. Pathology*, 46:135-146 (1964).
Tuncel, "Nonswellable and swellable ethylene glycol dimethacrylate-acrylic acid copolymer microspheres" *J. Polymer Sci.: Pt. A: Polymer Chem.* 34:45-55 (1996).
Van Wezel, "Growth of Cell-strains and Primary Cells on Microcarriers in Homogeneous Culture," *Nature*, 216:64-65 (1967).
Wein, "Pharmacology of Incontinence," *Urol. Clin. N. Am.*, 22:557-573 (1995).
Appell, "Injectables in the treatment of female stress incontinence" *Curr. Opin. Obstetrics Gynecol.*, 7:393-396 (1995).
U.S. Appl. No. 09/263,773; (U.S. Patent No. 6,335,028) Office Action Dated Jul. 19, 2000.
U.S. Appl. No. 09/263,773; (U.S. Patent No. 6,335,028) Office Action Dated Apr. 20, 2001.
U.S. Appl. No. 09/263,773; (U.S. Patent No. 6,335,028) Notice of Allowability Dated Aug. 17, 2001.
U.S. Appl. No. 09/528,990; (U.S. Patent No. 6,436,426) Office Action Dated Mar. 22, 2001.
U.S. Appl. No. 09/528,990; (U.S. Patent No. 6,436,426) Office Action Dated Oct. 29, 2001.
U.S. Appl. No. 09/528.990; (U.S. Patent No. 6,436.426) Interview Summary Dated Apr. 4, 2002.
U.S. Appl. No. 09/528,990; (U.S. Patent No. 6.436,426) Notice of Allowability Dated Apr. 9, 2002.
U.S. Appl. No. 09/528,990; (U.S. Patent No. 6,436,426) Supplemental Notice of Allowability Dated May 13, 2002.
U.S. Appl. No. 09/528,989; Office Action Dated Apr. 11, 2001.
U.S. Appl. No. 09/528,989; Office Action Dated Sep. 24, 2001.
U.S. Appl. No. 09/528,989; Office Action Dated Feb. 12, 2003.
U.S. Appl. No. 09/528,989; Office Action Dated Nov. 26, 2003.
U.S. Appl. No. 09/528,989; Notice of Allowability Dated Dec. 7, 2004.
U.S. Appl. No. 09/528,989; Office Action Dated Sep. 19, 2005.
U.S. Appl. No. 09/528,989; Office Action Dated Jan. 19, 2007.
U.S. Appl. No. 09/528,989; Office Action Dated Sep. 20, 2007.
U.S. Appl. No. 09/528,989; Office Action Dated Feb. 27, 2008.
U.S. Appl. No. 09/528,991; (U.S. Patent No. 6,660,301) Office Action Dated Aug. 27, 2001.
U.S. Appl. No. 09/528,991; (U.S. Patent No. 6,660,301) Office Action Dated May 21, 2002.
U.S. Appl. No. 09/528,991; (U.S. Patent No. 6,660,301) Notice of Allowability Dated Jul. 2, 2003.
U.S. Appl. No. 10/220,984; (U.S. Patent No. 7,338,657) Office Action Dated Aug. 24, 2005.
U.S. Appl. No. 10/220,984; (U.S. Patent No. 7,338,657) Office Action Dated Apr. 18, 2006.
U.S. Appl. No. 10/220,984; (U.S. Patent No. 7,338,657) Office Action Dated Jan. 10, 2007.
U.S. Appl. No. 10/220,984; (U.S. Patent No. 7,338,657) Notice of Allowability Dated Oct. 18, 2007.
U.S. Appl. No. 10/029,294; (U.S. Patent No. 7,060,298) Office Action Dated May 19, 2003.
U.S. Appl. No. 10/029,294; (U.S. Patent No. 7,060,298) Office Action Dated Mar. 24, 2004.
U.S. Appl. No. 10/029,294; (U.S. Patent No. 7,060,298) Office Action Dated Jan. 6, 2005.
U.S. Appl. No. 10/029,294; (U.S. Patent No. 7,060,298) Office Action Dated Aug. 23, 2005.
U.S. Appl. No. 10/029,294; (U.S. Patent No. 7,060,298) Notice of Allowability Dated Feb. 1, 2006.
U.S. Appl. No. 10/222,819; (U.S. Patent No. 6,790,456) Notice of Allowability Dated May 6, 2004.
U.S. Appl. No. 10/704,919; (U.S. Publ. No. 2004/0096514) Office Action Dated Mar. 19, 2007.
U.S. Appl. No. 10/704,919; (U.S. Publ. No. 2004/0096514) Office Action Dated Jan. 9, 2008.
U.S. Appl. No. 10/704,919; (U.S. Publ. No. 2004/0096514) Office Action Dated May 14, 2008.
U.S. Appl. No. 10/704,919; (U.S. Publ. No. 2004/0096514) Office Action Dated Feb. 3, 2009.

(56) References Cited

OTHER PUBLICATIONS

U.S. Appl. No. 10/704,919; (U.S. Publ. No. 2004/0096514) Notice of Abandonment and Interview Summary Dated Feb. 3, 2009.
U.S. Appl. No. 10/919,257 (U.S. Publ. No. 2005/0025708) Office Action Dated Oct. 31, 2008.
U.S. Appl. No. 10/919,257 (U.S. Publ. No. 2005/0025708) Office Action Dated Aug. 4, 2009.
U.S. Appl. No. 10/919,257 (U.S. Publ. No. 2005/0025708) Office Action Dated Mar. 16, 2010.
U.S. Appl. No. 10/919,257 (U.S. Publ. No. 2005/0025708) Office Action Dated Oct. 1, 2010.
U.S. Appl. No. 12/534,070 Office Action Dated Dec. 21, 2010.
Office Action dated Jun. 20, 2013 for U.S. Appl. No. 12/197,187.
Chowdhury R. et al., In: Advanced Research on Animal Cell Technology, A.O.A. Miller ed., Kluwers Acad. Press, 315-327 (1989).
Jiaqi, "A New Embolic Material: Super Absorbent Polymer (SAP) Microsphere and its Embolic Effects," Nippon Acta Radiologica 56(1): 19-24 (1996) [English Translation].
Shafik, "Intraesophageal polytef injection for the treatment of reflus esphagitis" Surgical Endoscopy 10:329-331 (1996).
Hori et al., 'A New Embolic Material: Super Absorbent Polymer (SAP) Microsphere and its Embolic Effects'. IVR, vol. 11, No. 3, pp. 75-81, 1996. With english abstract.
Office Action dated Feb. 2, 2011 for U.S. Appl. No. 12/197,187.
Notice of Abandonment dated Oct. 16, 2008 for U.S. Appl. No. 09/528,989.
Office Action dated Jun. 13, 2011 for U.S. Appl. No. 10/919,257.
Office Action dated Jan. 29, 2003 for U.S. Appl. No. 09/945,793.
Office Action dated Jul. 21, 2003 for U.S. Appl. No. 09/945,793.
Office Action dated Apr. 29, 2004 U.S. Appl. No. 09/945,793.
Office Action dated Aug. 2, 2004 for U.S. Appl. No. 10/133,177.
Notice of Allowance dated Feb. 18, 2005 for U.S. Appl. No. 10/133,177.
Notice of Allowance dated Sep. 29, 2011 for U.S. Appl. No. 10/919,257.
Notice of Allowance dated Jan. 9, 2012 for U.S. Appl. No. 10/919,257.
Office Action dated Jun. 8, 2011 for U.S. Appl. No. 12/534,070.
Office Action dated Sep. 24, 2001 for U.S. Appl. No. 09/528,989.
Office Action dated Apr. 10, 2006 for U.S. Appl. No. 09/528,989.
Restriction Requirement dated Sep. 28, 2010 for U.S. Appl. No. 12/197,187.
Jayakrishnan et al., 'Hydrogel Microspheres from Crosslinked Poly(methyl methacrylate): Synthesis and Biocompatibility Studies', Bull Mater Sci, vol. 12 No. 1, pp. 17-28, Mar. 1989.

\* cited by examiner

INJECTABLE MICROSPHERES FOR TISSUE CONSTRUCTION

CROSS REFERENCE TO RELATED APPLICATIONS

This application is a continuation of U.S. patent application Ser. No. 10/220,984, filed Dec. 12, 2002, now U.S. Pat. No. 7,338,657, which is a National Stage Entry of PCT/US01/08528, filed on Mar. 15, 2001, which claims priority from U.S. Provisional Application Ser. No. 60/190,542, filed Mar. 20, 2000, each of which is incorporated herein by reference in its entirety.

1. FIELD OF INVENTION

The present invention relates to injectable compositions comprising biocompatible, hydrophilic, non-toxic, and substantially spherical microspheres and mesenchymal stem cells useful for tissue construction and generation. The invention also relates to methods of tissue construction and generation, for the treatment of various tissues damages and defects, using the injectable compositions.

2. BACKGROUND OF THE INVENTION

Tissue damages and defects can be the results of many conditions, including, but not limited to, disease, surgery, environmental exposure, injury, and aging. Tissue damages defects also take on many forms, making the treatment of them account for a large part of health-care resources. Examples of organs and body parts where tissue damages and defects may occur are:

Cardiovascular
Heart, including coronary artery,
Angioplasty of coronary vessels,
Blood vessels
Spinal cord (neural and neuromuscular)
Orthopedic
Bone, cartilage, tendon, and ligament
Breast
Gastrointestinal
Liver, gallbladder, bile duct
Pancreas (diabetes)
Intestinal
Other
Urinary system including kidney
Skin
Hernia
Dental
Blood transfusions (units of blood)
See, *Science* 1993; 260: 920-26.

Treatment for tissue damage and defects has attracted resources from such diverse fields as medicine, chemistry, and engineering. The results of these efforts, however, have been both encouraging and disappointing. This is partly due to the fact that tissues are not only composed of different type of cells but also from different organs and body parts. Therefore, they have different characters and react differently to a method of treatment or a specific material.

One type of treatment for tissue damage and defects involves the implant of artificial devices to facilitate tissue repair and generation. For example U.S. Pat. Nos. 5,981,825 and 5,716,404 disclose anatomically specific and bioresorbable implant devices for facilitating the healing of voids in bone, cartilage, and soft tissue. Besides the fact that they are only suitable for certain types of tissue defects, these methods and devices are often intrusive and require surgical procedures, resulting in discomfort to the patients and even rejection by the body.

Another type of treatment for tissue damage is the emerging tissue engineering technique, which often employ the combination of artificial and biological approaches to facilitate the body's own effort to heal or generate new tissues. For example, U.S. Pat. No. 5,885,829 discloses methods for regenerating dental and oral tissues from viable cells using ex vivo culture on a structural matrix. The regenerated tissues may then be applied to patients in need of such tissue repair. Although this type of tissue engineering promises to provide effective tissue repair and construction for many tissue deficiencies, they often involve expensive, complex and intrusive procedures. And, despite the great effort and progress made in in vitro and ex vivo cell culture technique, the body's acceptance of engineered tissues is still unpredictable.

Methods of using cultured cells and/or extracellular matrix alone or combining with artificial devices have also been developed for tissue construction and generation. This type of treatment often involves the culture of cells and extracellular matrix and the implantation of them into the body thereof. For example, U.S. Pat. No. 5,919,707 discloses a method for the isolation and use of pre-chondrocytes from umbilical cord that gives rise to chondrocytes which produce cartilage for implantation to repair tissue deficiencies. U.S. Pat. No. 5,830,708 discloses methods for producing naturally secreted human extracellular matrix material which are useful for the repair of soft tissue and skin defects. Although this type of methods are less intrusive and may be modified to avoid the use of surgical procedures, they usually do not provide the necessary mechanical strength to facilitate more effective tissue generation. Further, by primarily relying on cultured cells and extracellular matrix, these methods also increase the risk of rejection by the body.

The development of techniques that enable the isolation, purification, and culturally expansion of stem cells has provided a potent new tool for tissue construction and generation. "Stem cell" is a term used to describe a "generic" cell that is capable of growing to become numerous types of other specialized cells that perform specific body functions (like brain cells, muscle cells, bone cells, or blood cells). The ultimate stem cell would thus be a fertilized human egg, which consists of one cell, but has the instructions and capability to become every different type of cell within the human body.

Next to the embryo would be the totipotent embryonic stem cell. Embryonic stem cells are undifferentiated cells that are unlike any specific adult cell. They have the ability to form any adult cell. Because undifferentiated embryonic stem cells can proliferate indefinitely in culture, they could potentially provide an unlimited source of specific, clinically important adult cells such as bone, muscle, liver or blood cells. Yet, despite recent development in isolation and culturing of embryonic stem cells, their application in tissue repair and generation is still far from practical.

Thus, scientists have turned their attention to the more "committed" stem cells, which are cells that are capable of becoming many types, but not all types, of cells. Some examples of these would be "hematopoietic" stem cells, which are capable of forming all types of blood cells, or "neuronal" stem cells, which are capable of forming all types of brain cells. Thus, for example, a hematopoietic stem cell could not be made to produce brain cells.

Stem cells that can divide into more than one types of other cells are called pluripotent stem cells. One specific line of pluripotent stem cells important to tissue construction and generation are stromal stem cells or mesenchymal stem cells.

Mesenchymal stem cells ("MSCs") are the formative pluripotent blast cells found, inter alia, in bone marrow, blood, dermis and periosteum that are capable of differentiating into any of the specific types of mesenchymal or connective tissues (i.e., the tissues of the body that support the specialized elements; particularly adipose, osseous, cartilaginous, elastic, and fibrous connective tissues) depending upon various influences from bioactive factors, such as cytokines. Studies have confirmed that MSCs are capable of being differentiated into bone, cartilage, muscle, fat, and connective tissue cells. See, e.g., Owen, *J. Cell Sci. Suppl.* 10:63 (1988).

MSCs, therefore, are the body's storehouse of potential spare parts. Inside the body, there are pockets of unspecialized MSCs, tucked into a variety of places, that can migrate to an injury and, responding to signals in the milieu, embark on a normal developmental pathway to become what's needed. They are not totipotent, as are embryonic stem cells, but pluripotent, capable of differentiating into bone, muscle, cartilage, and connective tissue and their derivatives. Neither are they as far along the developmental trajectory as hematopoietic stem cells used to replenish bone marrow, or the neural stem cells that researchers recently rerouted to produce hematopoietic cells. Thus, MSCs have become the focus of development efforts relating to tissue construction and generation.

For example, U.S. Pat. No. 5,226,914 discloses processes and devices for utilizing isolated and culturally expanded marrow-derived mesenchymal stem cells for treating skeletal and other connective tissue disorders. The '914 patent discloses a process of isolating and purifying marrow-derived mesenchymal stem cells prior to differentiation and then culturally expanding to produce a tool for skeletal therapy.

U.S. Pat. No. 5,906,934 discloses a method for growing articular cartilage or subchondral bone in a patient by administering certain mesenchymal stem cells seeded in a polymeric carrier suitable for proliferation and differentiation of the cells into articular cartilage or subchondral bone. Thus, for purposes of tissue construction and generation, mesenchymal stem cells are a practical source of potential supply of cells for many different types of tissues.

Tissue bulking techniques have also been used in tissue construction and generation. Liquid or semi-liquid preparations with various degrees of viscosity have been used for this purpose. An example is silk-elastin protein polymers from Protein Polymer Technologies, Inc. These preparations are injectable, but they have on or more of the following limitations: (1) the "protein polymers" are gradually displaced within the tissue in which it was originally injected, thereby reduce or eliminating the intended tissue repair effect; (2) the "protein polymers" are digested biologically, through the lymphatic system or by other means, thus causing possible adverse effects as well as reducing tissue repair effect; and (3) the "protein polymers" tend to form a continuous foreign mass within the tissue after injection thereof, impeding tissue construction and generation.

Prior to the present invention, microspheres have been manufactured and marketed for in vitro use in anchorage dependent cell culture. (Van Vezel, A. L., *Nature*, 216:64-65 (1967); Levine et al., *Somatic Cell Genetics*, 3:149-155 (1977); Obrenovitch et al., *Biol. Cell.*, 46:249-256 (1983)). They have also been used in vivo to occlude blood vessels in the treatment of arteriovascular malformation, fistulas and tumors (See, U.S. Pat. No. 5,635,215 to Boschetti et al.; Laurent et al., *J. Am. Soc. Neuroiol*, 17:533-540 (1996); and Beaujeux et al. *J. Am. Soc. Neuroial*, A:533-540 (1996)).

Further, direct implantation of cells into living tissues such as brain or liver to correct specific deficiencies has been attempted albeit with a number of failures. The major problems associated with direct cell transplantation are the long term viability of the cell transplant and the immunopathological as well as histological responses. Microparticles with cells attached on their surface have been used in some in vivo applications. Cherkesey et al., IBRO, 657-664 (1996), described the culture of adrenal cells on coated dextran beads and the implantation into mammalian brain to supplant some specific disorders related to 6-hydroxydopamine-induced unilateral lesions of the substantia nigra. The pre-attachment of cells to dextran microcarriers allowed for improved functions of the cells implanted into the brain. Also liver cells transplantation has been used to manage acute liver failure, or for the replacement of specific deficient functions such as conjugation of bilirubin or synthesis of albumin. For this purpose, an intrasplenic injection of hepatocytes grown on the surface of microspheres was performed (Roy Chowdhury et al., in: Advanced Research on Animal Cell Technology, A O A Miller ed., 315-327, Kluers Acad. Press, 1989).

Therefore, there is a great need for safe, biocompatible, stable and effective methods of tissue construction and generation. There is also a need for stable and biocompatible injectable composition for tissue repairing.

3. SUMMARY OF THE INVENTION

The present invention provides injectable compositions and methods of using the injectable compositions for tissue construction and generation for the treatment of various tissue and organ defects. Specifically, the invention provides injectable compositions comprising biocompatible, hydrophilic, non-toxic and substantially spherical microspheres associated with stem cells, particularly mesenchymal stem cells, and a biocompatible carrier. The composition is injectable through needles of about 18 to 26 gauge, preferably 24 to 26 gauge, thus the compositions can be used accurately and conveniently for the treatment. Further, the microspheres are not capable of being eliminated through the lymphatic or immune system after injection, providing long lasting bulking, treatment, and growth effects. The methods are also more efficacious due to both the tissue bulking effect of the microspheres and the tissue generation effect of the stem cells.

Stem cells useful in the present invention include stem cells that can be isolated and culturally expanded, such as hematopoietic stem cells and neuronal stem cells. Particularly useful for the present invention are mesenchymal stem cells. The mesenchymal stem cells used in the present invention can be isolated and purified using known methods. The origin of the mesenchymal stem cells can be of any source suitable for the methods of isolation and cultural expansion, such as from bone marrow, muscle cells, dermis, or connective tissue cells.

The purified and culturally expanded stem cells, particularly mesenchymal stem cells, according to the present invention, are then associated with injectable microspheres, which process may happen directly through direct interactions between the microspheres and the stem cells, or indirectly through mediation of one or more cell adhesion promoters. The microspheres of the present invention preferably comprise ionic charges on their surfaces. More preferably, the microspheres comprise cationic polymers and exhibit positive charges on their surfaces. The association of stem cells with the microspheres not only facilitates effective delivery of the stem cells to the site of tissue repairing, but also performs tissue bulking function, further increasing the tissue construction and tissue generation result.

In one preferred embodiment, the microspheres of the present invention comprise one or more elastomers, such as acrylic polymers, vinyl alcohol polymers, acrylate polymers, polysaccharides, and silicones. These microspheres are flexible and can be easily injected through 18 to 16 gauge needles and yet large enough not to be digested by the lymphatic or immune system.

In another preferred embodiment, the microspheres of the present invention are highly water absorbing and capable of swelling after injection and upon contact with physiological fluids at the site of the injection, thus become secured at the site of injection. This property of the microspheres enable them to be easily injected through 18 to 26 gauge needles yet large enough, due to the swelling, not to be digested by the lymphatic or immune system. The swellable microspheres of the present invention preferably comprise sodium acrylate polymer, acrylamide polymer, acrylamide derivative polymer or copolymer, sodium acrylate and vinyl alcohol copolymer, vinyl acetate and acrylic acid ester copolymer, vinyl acetate and methyl maleate copolymer, isobutylene-maleic anhydride crosslinked copolymer, starch-acrylonitrile graft copolymer, crosslinked sodium polyacrylate polymer, crosslinked polyethylene oxide, or mixtures thereof.

In a preferred embodiment, there is no aggregation or clumping of the microspheres in the injectable composition before and during injection. In addition, the injectable composition can contain one or more of therapeutic or prophylactic agent, radiopacifying agent, and contrast medium or other detectable substances to provide therapeutic and other benefits while performing tissue construction and generation.

The present invention further encompasses methods of tissue construction and generation in a mammal by administering a composition of biocompatible, hydrophilic, non-toxic and substantially spherical microspheres associated with stem cells, especially mesenchymal stem cells in a biocompatible carrier to the mammal. The composition is suitable to be delivered into the body by means of syringes, catheters, needles, or other means for injecting or infusing microspheres in a liquid medium. The microspheres of the composition are injectable through needles of about 18 to about 26 gauge and are not capable of being eliminated or digested through the mammal's lymphatic system.

The present method is not restricted to the construction or generation of any specific tissue or organ of the mammal, rather the methods are suitable for treating tissue defects in many parts of the mammal, including, but not limited to, heart, coronary vessels, blood vessels, spinal cord, bone, cartilage, tendon, ligament, breast, liver, gallbladder, bile duct, pancreas, intestinal tissues, urinary system, skin, hernia, vocal and dental tissues. The method is especially suitable for construction and generation of bone, cartilage, and connective tissues; particularly extremities such as arms, hands, legs and face.

Thus, a method of tissue construction and generation by administering the injectable composition extracorporeally into organs, components of organs, or tissues prior to their inclusion into said mammal's body, organs, or components of organs is also encompassed herein.

4. DETAILED DESCRIPTION OF THE INVENTION

The present invention provides a safe, effective, stable, and long lasting method of tissue construction and generation (regeneration) for the treatment of various tissue defects by using novel injectable compositions suitable for tissue construction and generation. The invention encompasses injectable compositions comprising biocompatible, hydrophilic, non-toxic and substantially spherical microspheres associated with stem cells, preferably mesenchymal stem cells, and a biocompatible carrier useful for tissue bulking. The invention further provides methods of tissue construction and generation by administrating the injectable composition to a mammal in need of treatment for tissue defects. The injectable compositions and methods of tissue construction and generation of the present invention are intended to encompass the following advantages: (1) non-intrusive and easy to administer, providing advantages over surgical procedures and methods using artificial devices; (2) facilitating tissue generation with mesenchymal stem cells and their differentiation into proper type of tissues being repaired; (3) good biocompatibility and thus reduced adverse reaction from the body; (4) the injected materials are not easily displaced within the tissues in which they were originally injected, thus achieving the intended tissue construction results without repeated administration or causing adverse side effects in the patient; (5) the injected materials are not readily digested, displaced, or eliminated either biochemically or through the lymphatic system, providing a more effective and longer lasting treatment; (6) the materials are of sufficient size to be injected through 18 to 26 gauge needles, allowing more accurate, efficacious and less intrusive delivery of the composition; (7) the injected particles are flexible, but not fragile, facilitating easy injection without being broken, providing easy and safe injection; (8) the injected particles are not irregularly shaped and do not clump together; and (9) the injected particles comprise may further comprise therapeutic or prophylactic agent, radiopacifying agent, and contrast medium or other detectable substances to provide therapeutic and other benefits while performing tissue construction and generation. These benefits, whether alone or in combinations, enhance the effectiveness of the treatment and are safe, more convenient and comfortable for patients.

As used in the present invention, "microspheres" means polymer or combinations of polymers made into bodies of various sizes. The microspheres can be in any shape, although they are often in substantially spherical shape. "Elastic microspheres" refers to microspheres comprise polymers that have elastic properties. Preferably, the elastic microspheres are capable to be compressed to up to 30% to 50% of their original shape. "Swellable microspheres" refers to microspheres that are capable of absorbing 5% or more water by weight, or increasing their dry weight to about 20 times of their original weight, upon hydration and other conditions and enlarge in size. Specific to the present invention, elastic or swellable microspheres means particles that are flexible enough so that they can be easily injected through needles of 18 to 26 gauge, yet the microspheres are not fragile so that they are not broken during the process of injection and are not capable of being digested or eliminated through the lymphatic system after injection.

The microspheres of the present invention also comprise particles that are "hydrophilic," which, as used in the invention, means the particles can dissolve in, absorb, or mix easily with moisture, water or aqueous solution. This characteristic is important in that it prevents the microspheres from clumping during the procedure.

"Substantially spherical" generally means a shape that is close to a perfect sphere, which is defined as a volume that presents the lowest external surface area. Specifically, "substantially spherical" in the present invention means, when viewing any cross-section of the particle, the difference between the average major diameter and the average minor diameter is less than 20%. The surfaces of the microspheres of the present invention appear smooth under magnification of up to 1000 times. Further, the microspheres of the present invention can be precisely calibrated so that their sizes can be accurately controlled. The microspheres of the present invention may comprise, in addition to the particles, other materials as described and defined herein.

"Tissue damage," and "tissue defects," are used interchangeably in the present invention. They refer to abnormal conditions in a mammal's tissue that are caused by internal and/or external events, including, but not limited to disease, surgery, environmental exposure, injury, aging, or combinations thereof.

"Tissue construction," "tissue generation," "tissue engineering" and "tissue repair," are used interchangeably in the context of the present invention and refer to the processes or events associated with the healing, growth, regrowth, or change of conditions of tissues. The tissues encompassed by the invention include, but not limited to, muscle tissues, connective tissues, fats, and, nerve tissues. The tissue defects suitable for the treatment of the present invention include, but not limited to, defects in mammal's heart, coronary vessels, blood vessels, spinal cord, bone, cartilage, tendon, ligament, breast, liver, gallbladder, bile duct, pancreas, intestinal tissues, urinary system, skin, hernia, and dental tissues.

"Injectable" as used in the present invention means capable of being administered, delivered or carried into the body via syringes, catheters, needles, and other means for injecting or infusing microspheres in a liquid medium.

"Cell adhesion promoter" in the present invention means any material that, because of their presence in or association with the microspheres, promotes or enhances the adhesiveness of cells to the surface of the microspheres. These materials are often proteins that are bound to the surface of the microspheres through covalent bonds of the proteins and the polymers.

"Therapeutic agent" in the present invention refers to any substance that provides therapeutic effects to the process of dermal augmentation or biological or physiological responses to the dermal augmentation. An example of therapeutic agent is an anti-inflammation agent that prevents or reduce the effect of inflammations associated dermal augmentation.

For clarity of disclosure, and not by way of limitation, the detailed description of the present invention is divided into the subsections which follow.

4.1 Injectable Compositions

The present invention provides an injectable composition suitable for tissue construction and generation for a mammal. Specifically, the suspension comprises biocompatible, hydrophilic, non-toxic and substantially spherical microspheres associated with stem cells, especially mesenchymal stem cells and a biocompatible carrier. The composition is injectable through needles of about 18 to 26 gauge and the microspheres are not capable of being digested, displaced or eliminated by the lymphatic or immune system. Thus, the injectable composition of the present invention comprise three major components: microspheres, mesenchymal stem cells and biocompatible carrier.

The pluripotent mesenchymal stem cells have the ability of taking different growth path upon receiving different signals. For example, in response to bone morphogenic factor, mesenchymal stem cells take on a bone forming lineage and eventually developed into bone cells. In response to injury, mesenchymal stem cells can migrate to appropriate site and react to local differentiation factors, thus adopting a distinct path. Thus, after the successful purification and cultural expansion of the mesenchymal stem cells, microspheres are associated with cells under conditions that will facilitate the differentiation of the stem cells at the site of injection and tissue repair. This can be achieved by the addition of known differentiation inducers or by the naturally generated inducers at the site of tissue injury.

The isolation, purification, and culture of mesenchymal stem cells used in the present invention can be achieved through methods known to those skilled in the art, such as the method described by Young et al., *J. Tiss. Cult. Meth.*, 14:85 (1992) or the method disclosed in U.S. Pat. No. 5,226,914, both are incorporated by reference as part of the disclosure herein. The origin of the mesenchymal stem cells can be of any source suitable for the methods of isolation and cultural expansion, such as from bone marrow, muscle cells, or connective tissue cells.

More specifically, and by way of example, it has been demonstrated that human mesenchymal stem cells can be isolated and purified from a number of different sources, including plugs of femoral, head cancellous bone pieces obtained from patients with degenerative joint disease during hip or knee replacement surgery, and from aspirated marrow obtained from normal donors and oncology patients who have marrow harvested for future bone marrow transplantation. Although the harvested marrow can be prepared for cell culture separation by a number of different mechanical isolation processes depending upon the source of the harvested marrow (i.e., the presence of bone chips, peripheral blood, etc.), the critical step involved in the isolation processes is the use of specially prepared media that contain agents which allow for not only mesenchymal stem cell growth without differentiation, but also for the direct adherence of only the mesenchymal stem cells to the plastic or glass surface area of the culture dish and, later on, the microspheres. The availability of special media that allow for the selective attachment of the desired mesenchymal stem cells, which are present in the marrow samples in very minute amounts, makes it possible to separate the mesenchymal stem cells from the other cells (i.e., red and white blood cells, other differentiated mesenchymal cells, etc.) present in the bone marrow.

Genetic and molecular studies have led to the commercial production of cell culture media that facilitate the division and growth of mesenchymal stem cells without differentiation, such as the $BGJ_b$ medium manufactured by Gibco (Grand Island, N.Y.), although modifications may be necessary based on the specific type of mesenchymal stem cells used. A person skilled in the art would understand and be able to perform the necessary modification.

The isolation and culturally expansion of mesenchymal stem cells typically start with the isolation of the stem cells from animal or human sources. Harvest from bone marrow is usually the preferred method. The harvest is performed typically by mixing marrow or pieces of bone with suitable media, such as $BGJ_b$ medium. After dispersing the marrow and spinning, a pellet of cells and bone pieces are obtained. Bone pieces are further removed through washing and spinning and the remaining cells are re-suspended in the medium. It is necessary, sometimes, to trypsinize and freeze the cells to kill any fibroblasts in the cell culture. The culturing of the stem cells in the medium then begins, which usually takes one to a few days for the cells to become confluent.

The confluent mesenchymal stem cells are then detached from their cultural expansion surface support, preferably by trypsinization, and associated with the microspheres of the present invention, which have superior cell adhesion ability. This process is similar to the conventional microbead culturing of mammal cells, except that particular medium cultural suitable for stem cell culturing is used. The association process is usually accomplished by mixing the microspheres in the cell culture. The microspheres will provide new surface for anchoring and continuing the culturing process of the stem cells. The microspheres may comprise cell adhesion promoters to further facilitate adhesion and growth of the stem cells on the microspheres. Various types of cell adhesion promoters well known in the art may be used in the present invention. In particular, cell adhesion promoters can be selected from collagen, gelatin, glucosaminoglycans, fibronectins, lectins, polycations (such polylysine, chitosan and the like), or any other natural or synthetic biological cell adhesion agent. Preferably, the cell adhesion promoter is present in the microspheres in an amount between about 0.1 to 1 g per ml of settled microparticles.

In another embodiment, the detached stem cells can be mixed with the sterilized microspheres immediately before injection, either inside a syringe or in a container and then transferred into a syringe. The microspheres can be either pre-swollen, as discussed below, or kept from swelling so that a desired full swollen size is achieved after injection. The mixture of microspheres and the stem cells is then ready to be injected into the body. After the microspheres and the stem cells reach the site of injection, the microspheres provide both anchorage support for the stem cells and structural support tissue repairing and regrowth.

Microspheres for use in the injectable composition are non-toxic to cells and tissues, biocompatible with the body's physiological conditions, hydrophilic, and substantially spherical. The microspheres comprise various polymers including biopolymers such as gelatin. In one embodiment, the microspheres comprise elastomers and, preferably, the elastomer are selected from the group consisting of acrylic polymers, vinyl alcohol polymers, acrylate polymers, polysaccharides, silicones, and mixtures thereof.

The elastic microspheres for use in the present invention may have diameters ranging between about 40 μm to about 500 μm. Preferably, the diameters are between 50 μm and 300 μm, most preferably, between 100 μm and 300 μm. These sizes are advantageous in that they enable the microspheres to be easily injectable through needles of 18 to 26 gauge to provide accurate and effective delivery of the injectable composition into the intended area, yet the microspheres are large enough so that they will not be digested, displaced, or eliminated by the lymphatic system.

The elastic microspheres for use in the present invention are flexible so that they can easily pass into and through injection devices without being broken or permanently altered in shape. The microspheres are also resistant to the muscle contraction stress generated during and after the injection process. Specifically, the microspheres of the present invention are easily injectable through needles of about 18 to 26 gauge. They are also thermally stable which allows for easy, convenient sterilization, and frozen storage for the preparation of injection.

In another embodiment, the microspheres of the present invention comprise crosslinked polymers that are highly water absorbing and, thus, capable of swelling upon contacting with physiological fluids in certain conditions. As understood by a person skilled in the art, the degree of swelling of crosslinked polymers generally depends on the properties of the polymeric materials such as their ionic character, the hydrophilicity of the polymeric materials, and the degree of crosslinking. Properties, such as salt and ionic concentration and level of pH, of the solvent in which the microspheres are suspended or with which the microspheres are contacting also affect the degree of swelling.

As disclosed herein, by carefully controlling the size and the degree of swelling of certain crosslinked and swellable polymers, safe, effective, and long lasting dermal augmentation can be achieved using these microspheres. According to the invention, polymeric materials having high water absorbing ability are first chosen. The swellability of these polymers can be further manipulated by controlling the polymer's ionic character and the degree of crosslinking by methods known to a skilled artisan.

The microspheres of the present invention can be either anionic or cationic. Preferably, cationic microspheres are used because of their superior ability of promoting cell adhesion. The crosslinking degree of the microspheres can be changed either chemically or through radiation. A variety of crosslinking agents may be used, including, but not limited to, tetraethylene glycol diacrylate, tetraethylene glycol dimethacrylate, ethylene glycol dimethacrylate, methacrylate, and pentaerythritol dimethacrylate. The microspheres of the invention may comprise from about 0.5% to about 20%, by molecular weight, of crosslinking agents. Preferably, the microspheres comprise from about 1% to about 5%, by molecular weight, of crosslinking agents.

More importantly, the present invention has discovered that the swelling of the microspheres comprising these polymers can be further controlled by controlling the solvent in which the microspheres are suspended. This is achieved through two steps as disclosed herein. First, the size of the microspheres before injection are carefully controlled by using appropriate solvents, salt concentration and pH level according to the specific microspheres used. The microspheres before injection may either remain in their original size or swell to certain degree due to their contact with the solvent. The pre-injection swelling is controlled so that the microspheres are easily injectable through 18 to 26 gauge needles. Second, after injection and upon contacting with tissues at injection site, the microspheres may further swell into predetermined size or retain their pre-injection size, either of which size will allow the microspheres to be secured at the site of injection and achieve desired tissue engineering effect. The degree of pre-injection swelling, and thus the after injection swelling, is determined by the particular microspheres used and the nature and location of the tissue defects being treated.

The swellable microspheres for use in the present invention have diameters range from about 10 to about 500 μm before swelling. Preferably, before swelling, the diameters of the microspheres are from about 10 to about 300 μm and, most preferably, from about 100 to about 300 μm. After injection and swelling, the microspheres have average diameters larger than about 40 μm, preferably larger than about 70 μm and, more preferably, larger than about 100 μm. The microspheres of the present invention are capable of swelling to about 4 times of their original diameters or about 15 times of their original volume. The full swollen size of the microspheres after injection are controlled, by various means discussed above, so that they are secured at the site of injection while not causing any potential injuries to the tissues. Further, the full swollen sizes of the microspheres after injection are predetermined based on factors such as the physiological conditions of the injection site, the original microspheres sizes, the solvent used and the pre-injection swelling of the microspheres. Thus, a specific injection plan can be designed according to the particular tissue repair need of the case. These sizes and properties of the microspheres are advantageous in that they enable the microspheres to be easily injectable through needles of 18 to 26 gauge, preferably 24 to 26 gauge, yet the microspheres are large enough so that they will be secured at the site of injection and will not be digested or eliminated by macrophage or other elements of the immune or lymphatic system.

The microspheres are also resistant to injection force created by 18 to 26 gauge needles and to the muscle contraction stress generated during and after the injection process. The microspheres are also thermally stable which allows for easy, convenient sterilization, and frozen storage for the preparation of injection.

Many types of crosslinked polymers having high water absorbing ability are suitable for use in the present invention as long as they are non-toxic to tissues and cells and are biocompatible. Preferably, the polymers are selected from the group consisting of sodium acrylate polymer, acrylamide polymers, acrylamide derivative polymers or copolymers, sodium acrylate and vinyl alcohol copolymer, saponification products of copolymer of vinyl acetate and acrylic acid ester, vinyl acetate and acrylic acid ester copolymer, vinyl acetate and methyl maleate copolymer, isobutylene-maleic anhydride crosslinked copolymer, starch-acrylonitrile graft copolymer and its saponification products, crosslinked sodium polyacrylate polymer, and crosslinked polyethylene oxide.

The invention encompasses non-swellable microspheres, or microspheres that do not significantly increase in volume or diameter upon injection, as well as swellable microspheres. The appropriate microspheres can be chosen dependent upon the tissue or organ defect to be treated.

The swellable microspheres of the present invention can be biodegradable or non-biodegradable. Preferably, the microspheres are sterilized before injection. They are also thermally stable which allows for easy, convenient sterilization, and frozen storage. The microspheres for use in the present invention are also stable in suspension which allows the microparticles to be formulated and stored in suspension and injected with different liquids or oils. More specifically, the hydrophilic nature of the microspheres permits placing them in suspension, and in particular, in sterile form of injectable solutions, while avoiding the formation of aggregates or adhesion to the walls of storage containers and implantation devices, such as catheters, syringes, needles, and the like.

The microspheres of the present invention may contain within their structure or on their surfaces other chemicals, therefore displaying particular properties, such as therapeutic, radio-pacifying, and contrasting effects; promotion of cell adhesion; and capability of being chemically modified.

The microspheres of the present invention may further associated with contrast medium or agent. Contrast media useful within the present invention can be found in Dawson et al. *Contrast Medium in Practice* (Springer-Verlag, 1994). Contrast media include, but not limited to, ultrasonic media, superparamagnetic media, and gadolinium contrast media. Preferably, the contrast media are any media that contain barium or iodine salts, such as high molecular weight salts, including acylamino-e-propion-amido-3-triiodo-2,4,6-benzoic acid, which can be prepared under the conditions described by Boschetti et al. (*Bull. Soc. Chim., No.* 4 France, (1986)). In the case of barium or magnetite salts, they can be directly introduced in powered form in the initial monomer solution.

Various types of cell adhesion promoters well known in the art may be used in the present invention. In particular, cell adhesion promoters can be selected from collagen, gelatin, glucosaminoglycans, fibronectins, lectins, polycations (such polylysine, chitosan and the like), extracellular matrix, degradation products of cells or tissues, or any other natural or synthetic biological cell adhesion agent.

Cell adhesion promoters or marking agents are introduced on microspheres by chemical coupling procedures well known in affinity chromatography, referred to by the term "ligand immobilization". Another method of introduction is by diffusion within the gel 2 network that constitutes the bead and then trapping the diffused molecules in place by precipitation or chemical cross-linking. Therapeutic agents, drugs or any other active molecules that are suitable for transportation by the beads can also be introduced into the microspheres prior to injection.

The microspheres of the present invention also can be chemically modified so that they will "carry" therapeutic effects, vascularization effects, anti-vascularization effects, visualization properties, anti-inflammatory effects, anti-bacterial effects, anti-histamine effects, or combinations thereof. The chemical modification of the microspheres of the present invention is made possible by the fact that the microspheres comprise particles made of polymers that are crosslinked so that they can contain chemicals within their structures that possess various properties and that they possess unique characteristics associated with surface covalent bonds.

Microspheres of the present invention further possess the property of non-aggregating, which usually results from an ionic charge of the microspheres. This allows easier injection and more effective tissue generation, especially in situations where cells are associated with the microspheres. This property is important to tissue generation of the present invention because it makes injection of the microspheres through 18 to 26 gauge needles possible and easier. This property of the microspheres also prevents them from aggregating or adhering to syringe or needle walls or other device used in the process.

Microspheres of the present invention can be prepared by suspension polymerization, drop-by-drop polymerization, or any other method known to the skilled artisan. The mode of microsphere preparation selected will usually depend upon the desired characteristics, such as microsphere diameter and chemical composition, for the resulting microparticles. The microspheres of the present invention can be made by standard methods of polymerization described in the art (see, e.g., E. Boschetti, *Microspheres for Biochromatography and Biomedical Applications. Part I, Preparation of Microbands* In: Microspheres, Microencapsulation and Liposomes, John Wiley & Sons, Arshady R., Ed., vol. 2, p171-199 (1999), which is incorporated herein by reference). Microspheres are prepared starting from an aqueous solution of monomers containing adhesion agents such as collagen (gelatin is a denatured collagen). The solution is then mixed with a non-aqueous-compatible solvent to create a suspension of droplets, which are then turned into solid gel by polymerization of monomers by means of appropriate catalysts. Microspheres are then collected by filtration or centrifugation and washed.

The microspheres of the invention can also be obtained by standard methods of polymerization described in the art such as French Patent 2,378,808 and U.S. Pat. Nos. 5,648,100 and 5,635,215 each of which is incorporated herein by reference. In general, the polymerization of monomers in solution is carried out at a temperature ranging between about 0° C. and about 100° C. and between about 40° C. and about 60° C., in the presence of a polymerization reaction initiator.

The injectable composition of the present invention preferably comprises the microspheres associated with mesenchymal stem cells in an amount from about 10% to about 90% by weight and the biocompatible carrier in an amount from about 10% to about 90% by weight. More preferably, the amount ranges from 10% to 50% by weight for microspheres and the stem cells and from 50% to 90% for biocompatible carrier. The relative amount of the microspheres and the carrier changes according to the need of the specific tissue repair performed, depending on factors such as size of needle used, type of microspheres and carriers used, type of tissue defect, area of injection, type of tissue or cells being repaired, and whether cells are associated with the microspheres prior to injection.

In one embodiment, the injectable composition of the invention comprises microspheres suspended in stem cell culture medium which also contain detached stem cells. The composition can either be allowed to continue the stem cells culture process so that the cells will be associated with the microspheres or the composition can be injected immediately. Thus, in this embodiment, the biocompatible carrier of the injectable composition is essentially the stem cell culture medium.

In another embodiment, the biocompatible carrier of the injectable composition is a solvent which has been used to control the swelling of the microspheres. In this embodiment, once the microspheres, the solvent and the detached stem cells are mixed together, the composition is immediately injected so that the viability of the stem cells are not affected.

Many types of emulsion and solvents can be used as the biocompatible carrier for the injectable composition. The solvent is preferably in such a condition that the microspheres can be uniformly suspended and, more importantly, that the swelling of the microspheres are also controlled by adjusting the solvent, the salt and ionic concentration, the pH value, or combinations thereof. Suitable solvents for the present invention include aqueous based solutions such as saline solutions, PBS solutions, alcohol based solutions, and other biocompatible hydro-organic solutions known in the art.

Salt concentration and pH level of the solvent can be changed to control the degree of swelling of the microspheres once they are suspended in the solvent. The presence of cations such as sodium, potassium, calcium, magnesium, iron, zinc, and ammonium has various level of effects on the degree of swelling of the microspheres depending on the specific polymer and salt used. The degree of swelling of the microspheres is partially controllable by changing the balance of smaller cations and larger cations between the solvent and the microspheres. In a preferred embodiment, the contrasting agent associated with the microspheres serves as an agent controlling the degree of swelling of the microspheres. A salt level of 0.01 M to 5 M is effective to keep the microspheres from swelling. While the microspheres swell uninhibitedly under a neutral pH level, the change of pH level will affect the degree of swelling. For the anionic microspheres, the preferred pH level to shrink the microspheres or to keep them from swelling is from about 0.1 to 5. For the cationic microspheres, a pH level ranges from about 6 to about 11 will shrink the microspheres or keep them from swelling.

Upon suspension in the solvent and before injection, the microspheres may swell and the degree of swelling is controlled by the solvent and other conditions, such as time and temperature of suspension. The pre-injection swelling of the microspheres is further determined by the desired after-injection-swelling for the microspheres. Thus, microspheres that have obtained high degree of swelling before injection will swell little after injection, whereas microspheres that have swelled little before injection will obtain a higher degree of swelling after injection. The size of the microspheres before, during and after injection is always controlled such that they are easily injectable through 18 to 26 gauge needles yet become secured at the site of injection.

The biocompatible carrier of the present invention can also be an emulsion. In this embodiment, the properties of the microspheres, especially their size and degree of swelling, are preserved through the well controlled balance between the aqueous and the non-aqueous phases in the emulsion.

To prepare a suspension of the microsphere and stem cells, dried sterilized microspheres are mixed with the desired solvent at a predetermined time such that the pre-injection swelling of the microspheres is controlled. Factors such as the material, size and crosslinking degree of the microspheres; the type, volume, salt concentration, pH level and temperature of the solvent; and the time of mixing are all considered before an injectable suspension is made and the injection is carried out thereafter. The stem cells can then be mixed with the suspension immediately before injection.

In a preferred embodiment, dried microspheres or pre-swelled microspheres, as described above, are mixed with medium containing detached mesenchymal stem cells. The suspension is then put into conditions for further culturing of the stem cells. During the culturing process, the microspheres may further swell depending on the conditions of the cultural medium and yet be easily injectable through needles of about 18 to 26 gauge, into all parts of the mammal in need of treatment without causing significant pain or discomfort.

4.2 Method of Tissue Construction and Generation

The invention provides methods of tissue construction and generation. The methods comprise administering a composition of biocompatible, hydrophilic, non-toxic and substantially spherical microspheres in a biocompatible carrier to a mammal. The method further specifies that the composition is injectable through a needle of about 18 to 26 gauge and the microspheres are not capable of being digested, displaced, or eliminated by the mammal's lymphatic system.

The various specific and preferred embodiments of the injectable compositions described in §4.1 can be used in the method for tissue construction and generation.

The tissue construction and generation method of the present invention provides the advantage of not being limited to the repair of any specific type of tissues or tissue defect in any specific organ or body part. Rather, the method is suitable for the construction and generation of defective tissues on any kind and of any parts of the body, including, but not limited to, heart, coronary vessels, blood vessels, spinal cord, bone, cartilage, tendon, ligament, breast, liver, gallbladder, bile duct, pancreas, intestinal tissues, urinary system, skin, hernia, and dental tissues. The invention's method reduces or eliminates immunological response to the rejection of the microspheres. Further the use of biocompatible, hydrophilic, non-toxic and substantially spherical microspheres and biocompatible carrier and the pluripotent mesenchymal stem cells improves tissue acceptance and the effectiveness of the treatment. The methods of the invention also have been shown to increase connective tissue response.

In a preferred embodiment of the present invention, the administration of the injectable composition comprises injecting the composition into the mammal in need of treatment. The injection can be carried out by conventional syringes and needles of 18 to 26 gauge. The injection can also be facilitated by various techniques such as endoscopic delivery or laparoscopic technique. Furthermore, when combined with the various advantageous embodiments of the injectable composition, such as autologous cells and therapeutic agents, the methods of the present invention provides additional and more beneficial therapeutic effects to further improve the tissue construction and generation.

The frequency and the amount of injection under the present invention is determined based on the nature and location of the particular case of the tissue defect being treated. Generally, because of the stable and long lasting character of the present invention's injectable composition, multiple injections are not necessary. In certain cases, however, repeated injection may be necessary to achieve optimal results. A skilled practitioner should be able to determine the frequency and the amount of the injection for each particular case.

According to the present invention, after injection, microspheres become secured at the position of the injection. The microspheres are not digested or eliminated by the lymphatic system. Furthermore, the microspheres will not displace or slide away from the position of injection. The affixation of the microspheres at the position of injection is due to, among other factors, their size, elasticity and flexibility, and hydrophilicity. The swellability of the microspheres at the site of injection is also important in helping secure the microspheres at the site of injection. Upon contacting the physiological fluids and the cells at the site of injection, the microspheres may further swell if there is no pre-injection swelling or the swelling is controlled to a lower level. The physiological condition, including salt concentration (e.g., sodium and potassium) and pH level, may further help the microspheres swell to the desired size.

This property of the microspheres allows precise control of the injection and makes it possible that the microspheres work together at position of injection and provide a scaffold for effective tissue construction and generation. In fact, the concept of using microspheres to provide a scaffold, rather than individual particles, for effective tissue construction and generation is a unique contribution of the present invention to the fields of tissue construction, tissue generation, and tissue engineering. The ability of forming a scaffold at the injection site makes the microspheres of the present invention particularly effective in providing tissue repair. The size of the scaffold is determined by the amount and frequency of the injection, which is in turn determined by the nature and location of the tissue construction and generation being performed. A skilled practitioner would appreciate the teaching of the present invention as a whole and be able to determine the exact amount and frequency of injection for each particular case.

The combination of the scaffold effect with the fact that microspheres of the invention preferably comprise mesenchymal stem cells, thus promoting new cell growth at the site of injection, makes the method of the invention particularly effective in providing a mechanism for tissue construction and generation. Since the microspheres of the invention are also preferably biodegradable, they can be incorporated into the repaired tissue after serving as scaffold for the tissue generation.

The present invention also provides method of construction and generation by injecting the injectable composition not directly into the body, but extracorporeally into organs, components of organs, or tissues prior to their inclusion into the body, organs, or components of organs.

The injection method of the present invention can be carried out by any type of sterile needles of 18 to 26 gauge and corresponding syringes or other means for injection, such as a three-way syringe. The needles, syringes and other means for injection are commercially available from suppliers such as VWR Scientific Products (West Chester, Pa.), Beckton Dickinson, Kendal, and Baxter Healthcare. The size of the syringe and the length of the needle used will dependent on the particular injection based on factors such as the specific disease or disorders being treated, the location and depth of the injection, and the volume and specific composition of the injectable suspension being used. A skilled practitioner will be able to make the selection of syringe and needle based on experience and 2 the teaching of the present invention.

The invention is further defined by reference to the following examples that describe in detail the preparation of injectable composition and the method of causing tissue bulking using the injectable composition. The following examples are illustrative only and should in no way limit the scope of the present invention. It will be apparent to those skilled in the art that many modifications, both to materials and methods, may be practiced without departing from the purpose and scope of this invention.

5. EXAMPLES

Example 1

58 grams of sodium chloride and 27 grams of sodium acetate were dissolved at room temperature in 100 ml of demineralized water. To this solution 400 ml of glycerol were added, the pH was adjusted to 6.0 and monomers were then dissolved. More specifically to this solution 90 gram of methylolacrylamide, 2 g of methacrylamidopropyl trimethyl-ammonium-chloride hydrochloride and 10 gram of N,N'-methylene-bis-acrylamide were added and the mixture was agitated until complete solubilization. The solution was heated at about 70° C. and 100 ml of a solution of gelatin at a concentration of 500 mg/ml was added. The total volume of the mixture was then adjusted to 1000 ml by addition of demineralized water. Finally 20 ml of 70 mg/ml ammonium persulfate aqueous solution and 4 ml of N,N,N',N'-tertam-ethyl-ethylene-diazrine was added. The obtained mixture was stored at 70° C. for about 3 hours until formation of a compact three-dimensional gel. This gel was totally insoluble in water. It was cut in small pieces and then ground to get very small particles of a dimension close to 100-200 μm. The particles were then suspended in 1 liter of physiological buffer containing 5% (w/v) glutaraldehyde and were shaken for two hours. Finally the particles were extensively washed to eliminate unpolymerized material, by-products and salts. To obtain homogeneous particle size distribution the particle suspension was sieved using an appropriate sieving net.

These particles possess the characteristics desired for tissue cell adhesion prior to muscle bulking and include cationic groups and adhesion agents for an effective cell adhesion mechanism.

Example 2

The solution of monomers prepared as described in Example 1 above was poured slowly into 1500 ml of stirred and hot paraffin oil (50-70° C.). After a few minutes a suspension/emulsion of liquids was obtained (the aqueous monomer solution was dispersed into oil and forms very small spherical droplets) and the polymerization occurred in suspension. The microdroplets were transformed into microbeads. The solid microbeads were recovered by centrifugation and suspended in 1 liter of physiological buffer containing 5% (w/v) glutaraldehyde and shaken for two hours. Finally the particles were extensively washed with water to eliminate completely the oil traces. Organic solvent extraction can be used for a more effective oil removal or an extensive washing in the presence of traces of nonionic detergents.

The obtained microbeads are calibrated if necessary by sieving through a nylon net and sterilized in an autoclave. These microspheres possess desired characteristics and properties for cell adhesion prior to muscle bulking.

Example 3

10 gram of styrene is mixed with 60 ml of toluene. 1 gram of divinylbenzene, 1 gram of dimethyl-aminoethyl-methacrylate and 1 gram of dimethyl-acrylamide are added to the resulting solution. After complete solubilization the monomer solution is mixed with 1% of AIBN (2,2'-azobisisobutyronitrile) as a polymerization catalyst and with 40 ml of paraffin oil as a viscosity inducer agent. The mixture is poured in an agitated water solution containing 0.5% Tween 80. In this situation there is formation of droplet suspension which turns into solid microbeads when the temperature is raised to 80-90° C. for three to five hours. The resulting beads are dried and organic solvents extracted. They are then swollen in an aqueous solution of collagen in phosphate buffer at neutral pH. Embedded collagen is then crosslinked with glutaraldehyde as described in Examples 1 and 2. The resulting beads possess cationic charges to interact with cell tissues and collagen for cell adhesion, and a chemotactic agent for cell growth and biocompatibility. They are suitable as tissue regeneration microspheres (i.e., to be used with stem cells).

Example 4

10 gram of silicone beads of a diameter of 20-300 μm are suspended in 30 ml of a solution of hexadecylamine (10 mg/ml) in ethylacetate. The suspension is stirred for two hours and 100 ml of ethanol is added. A 1 M ammonium sulfate or sodium chloride solution in water is added slowly until a 300 ml suspension is obtained. The amino-containing silicone beads are then reacted with a butanedioldiglycydylether in alkaline conditions. Epoxy derivatives are thus obtained on which gelatin is coupled using a method well known in the art. The resulting beads have the target properties of biocompatibility, hydrophilicity, non-biodegradability and cell adhesion by the presence of cationic amino groups and of gelatin as a cell growth promoting agent. They are suitable for tissue construction in accordance with the present invention.

Example 5

Beads prepared according to Example 2 were chemically activated with well known reagents used in the preparation of affinity chromatography sorbents. Activated beads were then used for the immobilization of cell adhesion agents such as fibronectin or vitronectin or laminin. Adhesion agents were dissolved at 1-10 mg/ml in a coupling buffer (100 mM carbonate or borate buffer pH 8 to 10) and the solution was mixed with the activated beads. The resulting beads possess the target properties of cell adhesion and growth, non-biodegradability and were non-resorbable. They are suitable for cell adhesion and permanent tissue construction in accordance with the present invention. Similarly, beads prepared according to Examples 3 and 4 can also be used.

Example 6

Microbeads commercially available under the name SPEC-70 (BioSepra Inc., Marlborough, Mass.) are polyacrylic polyanionic beads with elastic properties suitable for tissue bulking applications. However, these microbeads are not chemotactic and do not possess cationic charges. SPEC-70 microbeads are first drained under vacuum to eliminate water and then suspended in an aqueous solution of 1% chondroitin sulfate sodium salt in physiological conditions. Once this compound is absorbed on the bead structure, the beads are drained under vacuum and suspended in an aqueous solution containing 20% polylysine by weight. The suspension is shaken for a few hours and then drained under vacuum and rapidly washed with distilled water. The beads are then suspended in a solution of 5% butanedioldiglycidylether in ethanol and shaken overnight. Under these conditions, the polylysine is crosslinked as well as chondroitin sulfate. The resulting modified beads possess properties such as cationic charge for cell adhesion and promoting agents for cell growth such as polylysine and chondroitin sulfate.

Example 7

Microbeads from Examples 2 were drained under vacuum and then suspended in a saturated solution of barium chloride. They were shaken for two hours at room temperature and then drained under vacuum to eliminate the excess of barium chloride solution. The beads were suspended in a saturated solution of ammonium sulfate and shaken for two additional hours before elimination of the excess ammonium sulfate by vacuum filtration. This operation of contact with barium salts and ammonium sulfate can be repeated several times until the resulting radiopaque precipitate inside the beads reaches the desired amount. Resulting beads have radiopaque properties without having lost their initial desirable properties for tissue construction. The microbeads from Examples 3, 4 and 6 can be similarly used.

Example 8

Microbeads from Example 6 coated with polylysine are washed extensively with distilled water and suspended in a solution of sodium triazoate. The suspension pH is adjusted at about 7 by addition of acetic acid and shaken for several hours. The triazoate which is a radiopaque molecule is adsorbed tightly to the beads and the remaining reagents are eliminated by washing under vacuum. The resulting beads still possess cell promotion properties and now radiopacity as well.

Example 9

Microbeads described in the previous Examples may generate local temporary inflammatory reactions when injected in the target tissue. To avoid or decrease this phenomenon, the microbeads once coated with autologous cells can be filled with one or more anti-inflammatory drugs. The microbeads are cationic by their nature and can absorb anionic drugs by ion exchange effect.

Prior to injection microbeads are mixed with a 10 mg/ml anti-inflammatory anionic drug solution in sterile physiological saline. The suspension is shaken for several hours, and the beads filled with the drug are recovered by filtration or centrifugation. The resulting anti-inflammatory containing microbeads may then be used as tissue construction agents for use in the present invention.

Example 10

In order to assess the ability of polymeric beads from Example 2 to allow adhesion and growth of pre-adipocytes, fresh pre-adipocytes were collected and isolated from Wistar rat peri-epididymal fat tissue. Pre-adipocytes were then cultured in the presence of above described microbeads at a concentration of about $7.1 \times 10^5$ to about $1.7 \times 10^6$ cells/ml using the classical protocol for microcarrier culture in vitro. In a first phase the cells adhere on the bead surface and then they grow to totally cover the bead surface. The total colonization period is about 72 hours.

Pre-adipocytes from this type of culture show good growth and specific biological activity associated with differentiation into adipocytes (accumulation of lipids). Moreover these cells show the presence of specific enzymatic markers such as glycerol-3-phosphate-dehydrogenase and malate dehydrogenase. Microbeads having cells adhered thereto are useful for tissue construction for use in the present invention. The polymeric beads of Examples 2 to 5 can be similarly assessed.

Example 11

Preadipocytes and smooth muscle cells were isolated from Wistar rats according to a classical protocol to eliminate most of other contaminating cells. Separately these cells were cultured in a Petri dish in the presence of Dulbecco's Modified Eagle Medium supplemented with 10% fetal bovine serum. Gelatin-coated cationic microbeads prepared in accordance with Example 2 were added to cells cultured in vitro until they covered the surface of the Petri dish. Initial cell seed concentration was $0.7 \times 10^6$ cells/ml.

Repeated observations showed that cells adhered on the surface of microbeads and further multiplied to cover all the surface of the beads. After 5 to 7 days of culturing, there was formation of a solid network of beads where cells acted as a binder to consolidate the blocks of several beads. In most cases there were formation of solid non dissociable aggregates comprising beads and cells.

When, after a growing period (generally 5 to 7 days), a differentiating element such as 3,3',5-triiodo-D-thyronine was added to preadipocytes, the preadipocytes started to accumulate fats as micro-droplets within the cytoplasm.

Specific staining with 3,3'-dioctadecyloxacarbocyanine perchlorate or 2'-[4-hydroxyphenyl]-5-[4-methyl-1-piperazinyl]2,5'-bi-1H-benzimidazole demonstrated good adhesion of the cells on the bead substrate.

Staining of the cells with red oil at the beginning of the differentiating phase evidenced the accumulation of fats inside the cells.

In addition, specific enzymatic reactions of malic enzyme indicated that, at the end of the culture, resulting adipocytes were functionally viable with their major expressed characteristics. This enzyme is not expressed at the beginning of the culture and appeared simultaneously with the accumulation of fats.

Smooth muscle cells were also followed in their proliferation by DNA synthesis assay; their adhesion on the substrate was followed as per preadipocyte cells. Myocytes also showed good proliferation as well as adhesion on the beads.

Example 12

In order to assess the ability of polymeric beads from Example 2 to allow adhesion and growth of muscle cells, fresh smooth cell myocytes were collected from rat esophagus according to classical procedures. Cells were then cultured in the presence of above described microbeads at a concentration of about $10^6$ cells/ml using the classical protocol for microcarrier culture in vitro. In a first phase the cells adhered on the bead surface and then they grow until they cover the total bead surface. The total colonization period was about 72 hours.

Myocytes from this type of culture showed good growth and behavior and displayed the specific myosin marker. These microbeads having cells adhered thereto are useful for tissue bulking in accordance with the present invention. The beads from Examples 2 to 5 can be similarly assessed.

Example 13

At the issue of cell culture phase, the cell-bead particles are collected by filtration and washed extensively with blood serum from the host where the material is to be implanted. This operation ensures the elimination of foreign material from cell culture. The microbeads are then suspended in a few ml of autologous serum (a ratio of beads/serum is about 1:1) and are ready to be injected within the tissue to be bulked by means of an appropriate syringe or other injection device.

Example 14

Microbeads described in Example 2 are colonized with rat muscle cells according to Example 10 and conditioned according to Example 13 using rat serum diluted with physiological saline (50%-50%). The final sterile suspension of cells anchored on beads (50% of volume is constituted of beads and 50% of physiological saline) is injected in the right thigh muscle of a rat. Three months after bead injection the muscle was observed in its shape and histologically examined. Muscle volume should be larger than the left thigh muscle upon autopsy. Beads inside the muscle mass should appear surrounded by fibroblastic cells with no specific adverse inflammatory or necrosis effects.

Example 15

In a beaker containing 100 ml of demineralized water, 58 g of sodium chloride and 27 g of sodium acetate are dissolved. One adds 400 ml of glycerol and then the pH is adjusted between 5.9 and 6.1. Then 90 g of N-tris-hydroxy-methyl methylacrylamide, 35 mg of diethylaminoethylacryl-amide and 10 g of N,N-methylene-bis-acrylamide are added. One heats at 60-70 C and 100 mo of a hot 300 mg/ml gelatin solution is added. The total volume of the mixture is adjusted to 980 ml by addition of hot water and then 20 ml of a 70 mg/ml ammonium persulfate solution and 4 ml of N,N,N',N'-tetramethylethylenediamine are added.

This solution is poured into paraffin oil at 50-70 C stirring. After a few minutes, the polymerization reaction of acrylic monomers is manifested by an increase of temperature. The microspheres are then recovered by decanting, washed carefully, screened and sterilized in an autoclave in a buffered medium.

Those microspheres, after screen calibration, possess the characteristics desired for tissue regeneration (construction), including a marked cationic charge and an effective adhesion agent (gelatin or denatured collagen).

Example 16

The procedure of Example 15 is followed, using triethylaminoethyl acrylamide instead of diethylaminoethyl acrylamide. After recovery of the spheres, the gelatin is reticulated by means of a 25% glutaraldehyde solution (100 ml of all of the microspheres). The treatment is carried out stirring at 4 C overnight. It is followed by a washing with demineralized water.

Examples 17 and 18

The procedure of Examples 15 and 16 is followed, replacing 10 g of N-tris-hydroxymethyl methylacrylamide with 10 g of acrylic acid. The microspheres obtained possess high swellability that is controllable by salt and ionic concentration and pH level. Those microspheres are advantageously usable in direct view of the user at the time of handling.

Examples 19 and 20

The procedure of Examples 15 and 16 is followed, replacing N-tris-hydroxymethyl methylacrylamide with 10 g of N-acryloyl hexamethylene Procion Red HE-3B. The microspheres obtained possess an intense red coloration due to the integration of the acrylic dye in the polymer lattice. Those microspheres are advantageously usable in direct view of the user at the time of handling.

Examples 21 and 22

One hundred milliliters of microspheres obtained according to Examples 15 to 20 are washed with a 0.1 M borate buffer of pH 8 and then suspended in 50 ml of a 5 mg/ml rhodamine isothiocyanate solution. The suspension is then stirred for at least 15 hours, after which it is washed with a neutral buffer to a colorless supernatant.

Those fluorescent red-colored microspheres are then calibrated and sterilized, and can be used in tissue construction.

Examples 23 and 24

The procedure of Examples 15 to 20 is followed, replacing 10 g of N-tris-hydroxymethyl methylacrylamide with 10 g of a monomer opaque to X-rays, (acrylamido-3-propionamido)-3-triiodo-2,4,6-benzoic acid.

The microspheres obtained possess the property of absorbing X-rays and are therefore of particular interest in their in vivo follow-up after tissue construction.

Examples 25 to 28

The procedure of Examples 15 to 16 is followed, adding to the initial monomer solution 5 g of a radio-opaque soluble linear polymer, acrylamino-3-triiodo-2,4,6-benzoic polyacid (Examples 11 and 12) or (acrylamino-3-propionamido)-3-triiodo-2,4,6-benzoic polyacid (Examples 13 and 14).

Those polymers, having a molecular weight exceeding 100,000 Dalton, are imprisoned in the polymer lattice and, without disturbing the general properties of the microspheres for the applications claimed, make it possible to attain a radiopacity usable for the in vivo follow-up of tissue construction procedure.

Examples 29 and 30

The procedure of Examples 15 and 16 is followed, adding to the initial monomer solution 200 g of barium sulfate power. The microspheres obtained are opaque to both visible light and X-rays.

Examples 31 and 32

The procedure of Examples 15 and 16 is followed, adding 50 mg of magnetite ($Fe_3O_4$) to the initial monomer solution.

The microspheres obtained have the property of being detected in (Magnetic Resonance Imaging) MRI imagery.

Example 33

Comparative Evaluation of Two Types of Nonresorbable Spheres

The study consisted of injecting two types of calibrated microspheres, some prepared according to Example 2, the others of polystyrene (Biosilon Nunc Danemark), in pulmonary arterial vascularization of the rat and of observing on days 0, 8 and 30 the extent of the cell reaction and the remodeling modalities of the occluded vessels.

The study revealed four important facts:
  placement in suspension and vascular injection of the polystyrene spheres is difficult and clusters are formed at the segmental narrowing constituting the nozzle of the syringe, the base of the catheter and the possible changes of diameter of the catheters;
  the cell reaction is earlier, more intense and more durable with the spheres of Example 1 than with polystyrene. On the 8th day the thickness of the cell reaction covering the spheres of the invention is almost three times greater than that covering the polystyrene spheres (34 µm as compared to 13 µm);
  there is no differences in kinetics in the vascular remodeling with either material;
  no phenomenon suggesting the toxicity of either material was observed.

In conclusion, the microspheres of the invention are more manageable and more effective as adhesive agent.

Example 34

Preparation of Injectable Suspension

Microspheres from any of Example 2, 6, or 15-18 are washed, sterilized, and then mixed with cell culture containing mesenchymal stem cells. The stem cells are then detached from their original culturing surface, preferably by trypsinization. The mixture of microspheres, stem cell culture medium and detached stem cells is allowed to continue a culturing process that is both sterile and suitable for stem cell culturing for a period of no less than 12 hours. The suspension is then ready for injection.

The embodiments of the present invention described above are intended to be merely exemplary and those skilled in the art will recognize, or be able to ascertain using no more than routine experimentation, numerous equivalents to the specific procedures described herein. All such equivalents are considered to be within the scope of the present invention and are covered by the following claims.

The contents of all references described herein are hereby incorporated by reference. Other embodiments are within the following claims.

What is claimed is:

1. An injectable composition suitable for tissue construction and generation in a mammal which comprises swellable, biocompatible, hydrophilic, non-toxic and substantially spherical microspheres comprising stem cells and a biocompatible carrier, wherein the microspheres comprise at least one of the following: a sodium acrylate and vinyl alcohol copolymer, a vinyl acetate and acrylic acid ester copolymer, a vinyl acetate and methyl maleate copolymer, and a isobutylene-maleic anhydride crosslinked copolymer, wherein the composition is injectable through needles of about 18 to about 26 gauge and said microspheres are not capable of being displaced, or eliminated by the lymphatic system.

2. The composition of claim 1, wherein the stem cells are mesenchymal stem cells isolated from bone marrow, muscle tissues, dermis, or combinations thereof.

3. The composition of claim 1, wherein the microspheres have diameters ranging from about 10 µm to about 500 µm before injection.

4. The composition of claim 3, wherein the microspheres have diameters ranging from about 40 µm to about 300 µm before injection.

5. The composition of claim 4, wherein the microspheres have diameters ranging from about 100 µm to about 300 µm before injection.

6. The composition of claim 1, wherein the composition comprises the microspheres in an amount from about 10% to about 90% by weight and the biocompatible carrier in an amount from about 10% to about 90% by weight.

7. The composition of claim 6, wherein the composition comprises the microspheres in an amount from about 10% to about 50% by weight and the biocompatible carrier in an amount from about 50% to about 90% by weight.

8. The composition of claim 1, wherein the composition is a suspension of said microspheres in said biocompatible carrier.

9. The composition of claim 1, wherein the biocompatible carrier is an emulsion.

10. The composition of claim 1, wherein the biocompatible carrier is organic or non-aqueous solvent.

11. The composition of claim 1, wherein the biocompatible carrier is an aqueous based solution, a hydro-organic solution, or mixtures thereof.

12. The composition of claim 1, wherein the biocompatible carrier is a medium suitable for mesenchymal stem cell culturing.

13. The composition of claim 1, wherein the microspheres swell upon contact with physiological fluids.

14. The composition of claim 1, wherein diameters of the microspheres after injection are about 1 to 4 times greater than the diameters of the microspheres immediately prior to injection.

15. The composition of claim 1, wherein the composition is biodegradable.

16. The composition of claim 1, further comprises therapeutic agent, radio-pacifying agent, contrast medium, or mixtures thereof.

17. The composition of claim 16, wherein said agents or medium are bound to the microspheres.

18. The composition of claim 16, wherein the therapeutic agent is anti-inflammatory agent.

19. The composition of claim 1, wherein the microspheres are capable of being chemically modified to have therapeutic effects, vascularization effects, anti-vascularization effects, visualization properties, anti-inflammatory effects, anti-bacterial effects, antihistamine effects, or combinations thereof.

20. A method of tissue construction and generation in a mammal comprising administering to said mammal a therapeutically effective amount of a composition of swellable, biocompatible, hydrophilic, non-toxic and substantially spherical microspheres comprising stem cells in a biocompatible carrier, wherein the microspheres comprise at least one of the following: a sodium acrylate and vinyl alcohol copolymer, a vinyl acetate and acrylic acid ester copolymer, a vinyl acetate and methyl maleate copolymer, and a isobutylene-maleic anhydride crosslinked copolymer, wherein the composition is injectable through needles of about 18 to about 26 gauge and the microspheres are not capable of being displaced, or eliminated by the immune system.

21. The method of claim 20, wherein the stem cells are mesenchymal stem cells isolated from bone marrow, muscle tissues, dermis, or combinations thereof.

22. The method of claim 20, wherein the administration comprises injecting said composition into the mammal.

23. The method of claim 20, wherein the tissue construction and generation is for the treatment of tissue defects in the mammal's heart, coronary vessels, blood vessels, spinal cord, bone, cartilage, tendon, ligament, breast, liver, gallbladder, bile duct, pancreas, intestinal tissues, urinary system, skin, hernia, vocal cord, dental tissues, or combinations thereof.

24. The method of claim 20, wherein the mammal is a human.

25. The method of claim 20, wherein the administration comprises injecting said composition extracorporeally into organs, components of organs, or tissues prior to their inclusion into said mammal's body, organs, or components of organs.

26. The method of claim 20, wherein the composition is injected directly into the site in need of tissue repair.

27. A method of tissue construction and generation in a mammal comprising administering to said mammal a therapeutically effective amount of a composition of biocompatible, hydrophilic, non-toxic and substantially spherical microspheres comprising stem cells in a biocompatible carrier, wherein the microspheres comprise at least one of the following: a sodium acrylate and vinyl alcohol copolymer, a vinyl acetate and acrylic acid ester copolymer, a vinyl acetate and methyl maleate copolymer, and a isobutylene-maleic anhydride crosslinked copolymer, wherein the composition is injectable through needles of about 18 to about 26 gauge and the microspheres are not capable of being displaced, or eliminated by the immune system, and wherein a scaffold is formed when the microspheres are injected into the mammal.

* * * * *